United States Patent [19]
Vander Heyden

[11] Patent Number: 6,058,761
[45] Date of Patent: May 9, 2000

[54] MEASUREMENT OF RELATIVE DENSITY OF COMBUSTIBLE GASES

[75] Inventor: William H. Vander Heyden, Mequon, Wis.

[73] Assignee: Badger Meter, Inc., Milwaukee, Wis.

[21] Appl. No.: 09/016,029

[22] Filed: Jan. 30, 1998

[51] Int. Cl.[7] .................................................. G01N 9/00
[52] U.S. Cl. ........................................ 73/32 R; 73/30.01
[58] Field of Search .......................... 73/32, 23.2, 23.31, 73/30.01, 30.02, 23.28, 24.05; 374/37

[56] References Cited

U.S. PATENT DOCUMENTS

| | | | |
|---|---|---|---|
| 4,359,284 | 11/1982 | Kude et al. ................................ | 374/37 |
| 4,527,418 | 7/1985 | Arcara ......................................... | 73/30 |
| 4,677,841 | 7/1987 | Kennedy ..................................... | 73/30 |
| 4,934,178 | 6/1990 | Jones ....................................... | 73/32 R |
| 5,288,149 | 2/1994 | Meyer ....................................... | 374/36 |
| 5,307,668 | 5/1994 | Vander Heyden ..................... | 73/30.02 |
| 5,482,679 | 1/1996 | Dijkstra et al. ............................ | 422/94 |
| 5,635,626 | 6/1997 | Hammond et al. ...................... | 73/23.2 |

FOREIGN PATENT DOCUMENTS 0 591 639 A2   7/1993   European Pat. Off. .

OTHER PUBLICATIONS

European Search Report dated May 18, 1999 for PCT/US99/00169.

*Primary Examiner*—Hezron Williams
*Assistant Examiner*—Thuy Vinh Tran
*Attorney, Agent, or Firm*—Quarles & Brady LLP

[57] ABSTRACT

The relative density of a sample of a supply gas under test is determined by measuring an atmospheric pressure and a pressure differential for the reference gas and the sample gas as each is passed through a small orifice (16) with smooth walls, such as a pore formed in a sapphire jewel. The pressure measurements are made on a time base determined during the reference gas cycle. A microcontroller (15) then computes a relative density for the sample gas based on a known relative density for the reference gas and a ratio of pressure factors for the sample gas and the reference gas in a system operating at in a range from about 1 to about 6 psig.

22 Claims, 4 Drawing Sheets

MEASUREMENT OF RELATIVE DENSITY OF COMBUSTIBLE GASES

TECHNICAL FIELD

The field of the invention is methods and apparatus for determining the relative density of gases.

DESCRIPTION OF THE BACKGROUND ART

Control and reporting for combustible gases such as natural gases or industrial gas mixtures is necessary to assure the quality and usefulness of the gas to a user. While this is sometimes accomplished using composition analysis such as from a gas chromatography and by other methods, it is often sufficient to just determine the relative density of the gas as a basis for control and reporting. Natural gas, primarily methane with dilute mixtures of other gases, is a preferred fuel for energy generation or heat generation because it is clean and efficient.

In many countries, gas for use in households and industries is not available from long distance natural gas pipelines. In these instances, industrially produced gases such as propane and butane are mixed for distribution in local distribution systems. In some cases, natural gas is available, but in limited supply. Mixtures of propane and butane are then used for peak shaving of the natural gas supply. In still other situations, gas which is represented to be propane contains butane in some amount. In order to use such industrially produced gases for residential and industrial fuel, it is necessary that the composition and relative density of the gas be controlled. This is accomplished by measuring the relative density of the mixed gases and controlling the proportion of air in the mixture to adjust relative density of the overall mixture. This prevents the gas from being supplied to customers in a mixture that is too rich or too lean.

In such blending systems, mixing to a consistent Wobbe Index (the ratio of heating value to the square root of relative density) is the operating goal. When the supply gas relative density is known, relative density and heating value are sufficiently related to make it possible to control the blending of the product using only the relative density measurement.

Many local distribution systems for such gases operate at pressures of just 5 to 6 psig. Therefore, whether the fuel gas mixture includes methane or includes propane, butane and air, the relative density measurements should be made at that pressure or a lower pressure to avoid requiring an expensive gas compressor.

The measurement of the relative density of gases has been carried out using several methods and instruments. One instrument has a construction similar to a laboratory balance for measuring a ratio of the weight of a sample gas to the weight of air. The relative density of gases is related to air which is assigned a relative density of 1.0.

Another device for measuring relative density spins a volume of gas and a volume of air in sequential fashion and measures the weight in known volumes. Spinning enhances the sensitivity of the instrument since rotational acceleration increases the forces involved in the weight measurement.

Kennedy, U.S. Pat. No. 4,677,841, discloses a method and apparatus for determining relative density in which a small orifice is formed by a pore of 0.0025 inches in a sapphire jewel. Gas is flowed through the orifice and the rate of change of pressure across the orifice and used to calculate relative density. Kennedy disclosed that at a certain magic pressure, about 11 to 13 psig, the discharge coefficient of the pore can be ignored. While this is an acceptable method for methane and mixture of dilute fractions with methane, which have a relative density less than 1.0 (less than air), it has not proved suitable for use with propane and butane, which have a relative density greater than 1.0 (greater than the density of air). In addition, the method is subject to short term uncertainties because of the use of rate of change for measurement. Blending requires quick response to changes to maintain stability in control.

SUMMARY OF THE INVENTION

The invention relates to apparatus and methods for measuring relative density of gases such as methane, ethane, propane and butane alone or mixed together and mixed with air in a system utilizing relatively low pressures.

The invention determines relative density using discharge pressures measured at a common elapsed time for a reference gas and a sample gas as the gases are allowed to discharge from a volume chamber and through a small, precisely formed orifice. The relative density of the reference gas is known. This known value is then multiplied by a ratio of a gage pressure across the orifice for the sample gas to a gage pressure across the orifice for the reference gas to arrive at the relative density for the sample gas, assuming a common initial pressure for each of the gases prior to discharge.

In the method of this invention, the elapsed time of a reference gas is measured as a volume of reference gas is discharged until the reference gas reaches a preselected gage pressure. The gage pressure of a sample gas is then detected across the orifice for the same elapsed time period of discharge as determined for the reference gas.

One object of the invention is to provide relative density measurements using a reference gas to frequently correct the measurement apparatus.

Another object of the invention is to provide a method and apparatus for use with various types of gases which can be grouped according to isentropic properties.

Another object of this invention is to produce a rapid response with small short time uncertainty by eliminating use of rates of change of pressure.

Other objects and advantages, besides those discussed above, will be apparent to those of ordinary skill in the art from the description of the preferred embodiment which follows. In the description, reference is made to the accompanying drawings, which form a part hereof, and which illustrate examples of the invention. Such examples, however, are not exhaustive of the various embodiments of the invention and, therefore, reference is made to the claims which follow the description for determining the scope of the invention.

DETAILED DESCRIPTION OF THE PREFERRED EMBODIMENTS

Figure 1:
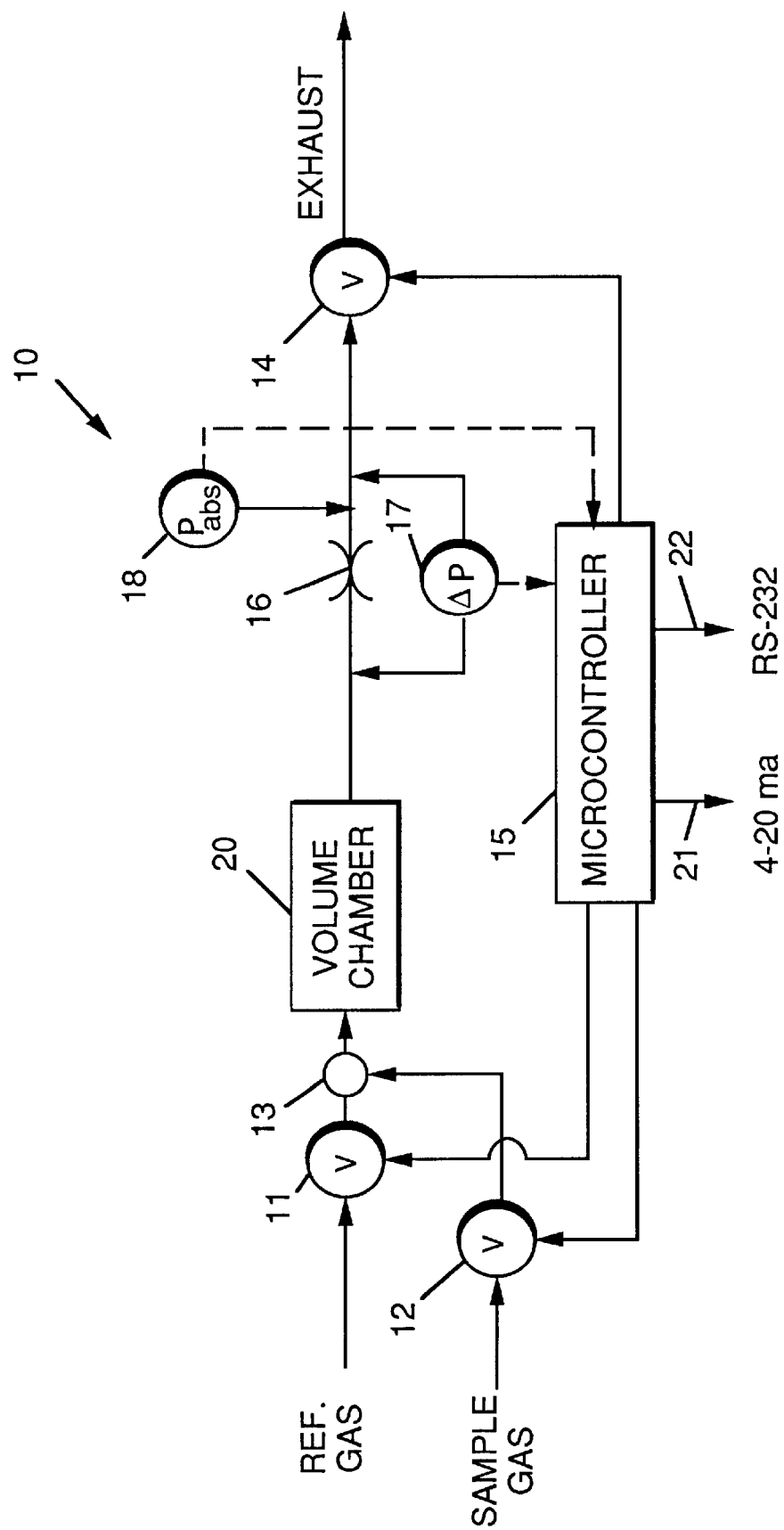
FIG. 1 is a block diagram of an apparatus for practicing the method of the present invention.

Referring to FIG. 1, a first embodiment of an apparatus for practicing the method of the invention uses a fixed volume chamber 20 to capture and release volumes of gas for measurement. A reference gas is admitted to volume chamber 20 though an on-off valve 11 connecting a supply of reference gas to an inlet on the chamber 20 through junction 13. A sample gas is admitted to the volume chamber 20 through an on-off valve 12 and through junction 13, which may be a T-fitting or a Y-fitting. Valves 11 and 12 are solenoid-controlled valves which are operated by signals from a microelectronic controller circuit represented by microcontroller 15. The supply gas and reference gas can also be connected separately to two inlets on the volume chamber making junction 13 unnecessary. Various equivalent circuits known in the art and involving various combinations of valves, supply lines and mixing chambers can be used in preparation for supplying the reference gas and the supply gas to volume chamber 20.

Gas is released from an outlet of the volume chamber 20 through an orifice 16 and through valve 14, which is also a solenoid-controlled on-off valve controlled by signals from the microcontroller 15. The orifice 16 is of the type disclosed in Kennedy, U.S. Pat. No. 4,677,841, described above. This orifice 16 is formed with a pore in a jewel body of relatively small size, which is in the range from about 0.0012 inches to about 0.0047 inches. Such an orifice 16 must have smooth walls so that a gas flowing through the orifice flows in an isentropic condition. The pore is preferably mounted in a structure having a diameter at least three times the diameter of the pore.

The orifice flow equation describes the molar flow rate as follows:

$$n(t) = \frac{KYC_D d^2}{\sqrt{M}} \sqrt{\frac{P\Delta P}{ZRT}} \quad \text{Eq. 1)}$$

where Y is the expansion factor,
K is the engineering units constant,
$C_D$ is the discharge coefficient,
d is the orifice or pore diameter,
M is the molecular weight of the gas,
P is the total inlet pressure of the gas,
$\Delta P$ is the gage pressure across the pore or orifice,
Z is the compressibility of the gas,
R is the gas constant, and
T is the absolute temperature.

In Eq. 1 above, the predicted flow rate is inversely related to the square root of the molecular weight. In large orifices, the value of $YC_D$ is dominated by Reynold's Numbers. In small or pore-sized orifices, the value of $YC_D$ becomes composition and pressure dependent leading to an almost linear change in the product, $YC_D$ but having a different slope and intercept point defining the linear change for each composition. It is this relationship that allows the prediction of relative density of natural gases and industrially produced gases such as propane and butane mixed with air, when proper pressure conditions are utilized according to the following Eq 2.

$$\frac{RD_s}{RD_r} = \left(\frac{Z_{ro}}{Z_{so}}\right)\left(\frac{\Delta P_s}{\Delta P_r}\right) \quad \text{Eq. 2)}$$

where:
$RD_s$=relative density of a sample gas,
$RD_r$=relative density of a reference gas,
$\Delta P_s$=a gage pressure across the orifice for the sample gas at the measurement time,
$\Delta P_r$=a gage pressure across the orifice for the reference gas at the measurement time,
$Z_{ro}$=the compressibility of the reference gas at standard conditions, and
$Z_{so}$=the compressibility of the sample gas at standard conditions.

Figure 4:
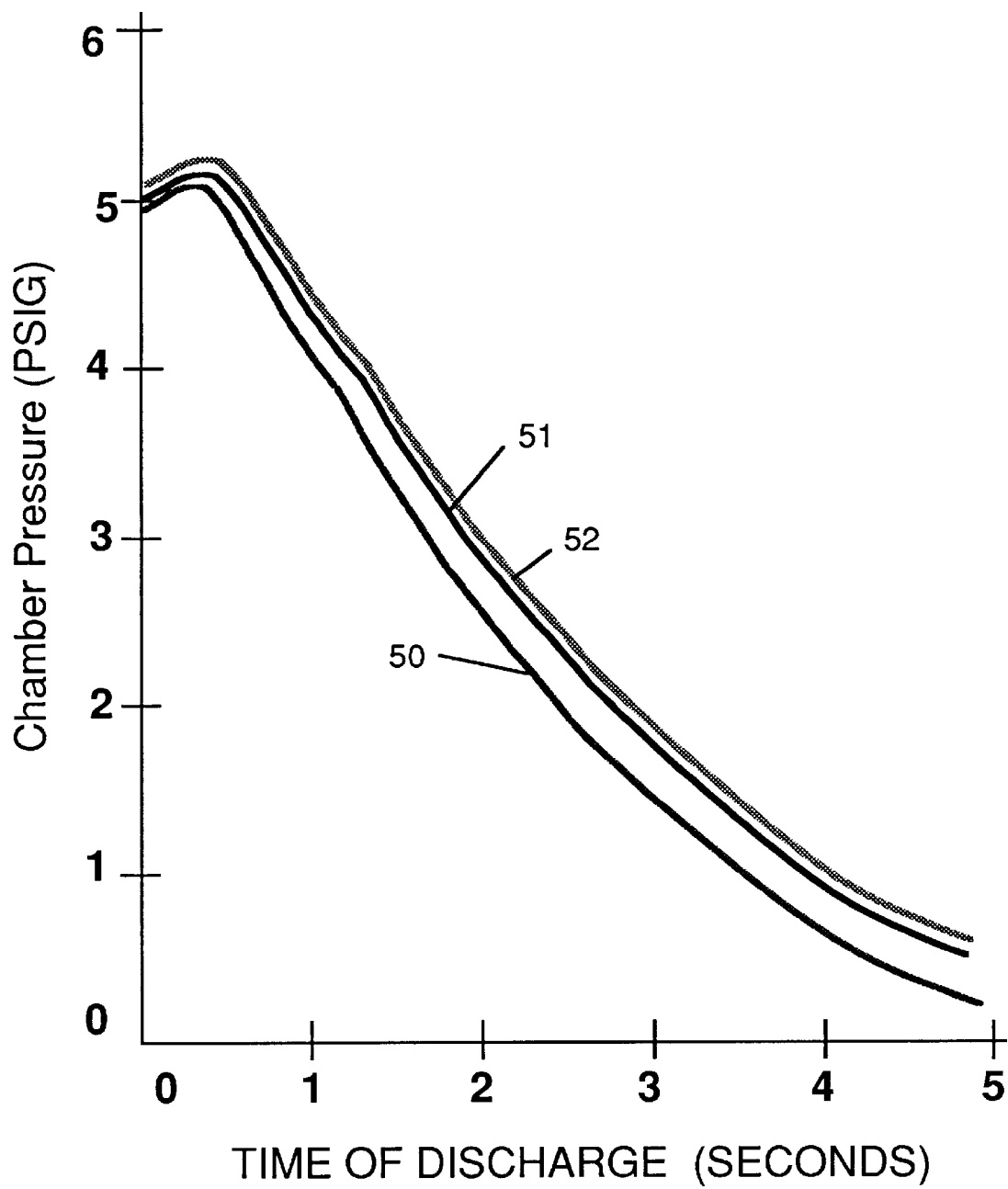
FIG. 4 is a graph of chamber pressure versus time within the apparatus of FIGS. 1 and 2.

FIG. 4 (not to exact scale) shows typical pressure decay discharge curves 50, 51 and 52 for air, carbon dioxide and propane, respectively. The graph in FIG. 4 plots the pressure in volume chamber 20 vs. the time during which the outlet valve 14 is open for release of the gas from the volume chamber 20.

For a selected chamber volume and a selected pore diameter as illustrated in FIG. 4 and in the region of four seconds in time of discharge, it has been found that the relative densities of air, carbon dioxide and propane follow the relationship stated in Eq. 2 above. The initial pressure in the chamber 20 is 5 psig.

It has also been found that most natural gas compositions are also measurable with a chamber initial pressure of about 1.5 psig.

When the sample gas is a mixture that includes methane or a mixture that includes propane or butane, the reference gas has a pressure ratio of measurement pressure to an initial chamber pressure of between 0.05 and 0.35.

Returning to FIG. 1, after the gas passes through the orifice 16, it is discharged as exhaust from the apparatus 10. An absolute pressure transducer 18 detects the atmospheric pressure and signals representing the atmospheric pressure are an input to the microcontroller 15. A differential or gage pressure transducer 17 is connected to the inlet and outlet of the orifice 16 to measure the pressure differential ($\Delta P$) across the orifice 16. The use of a single absolute pressure transducer is easily possible, but for explanation purposes, the separate gage and absolute transducer are shown.

Figure 3:
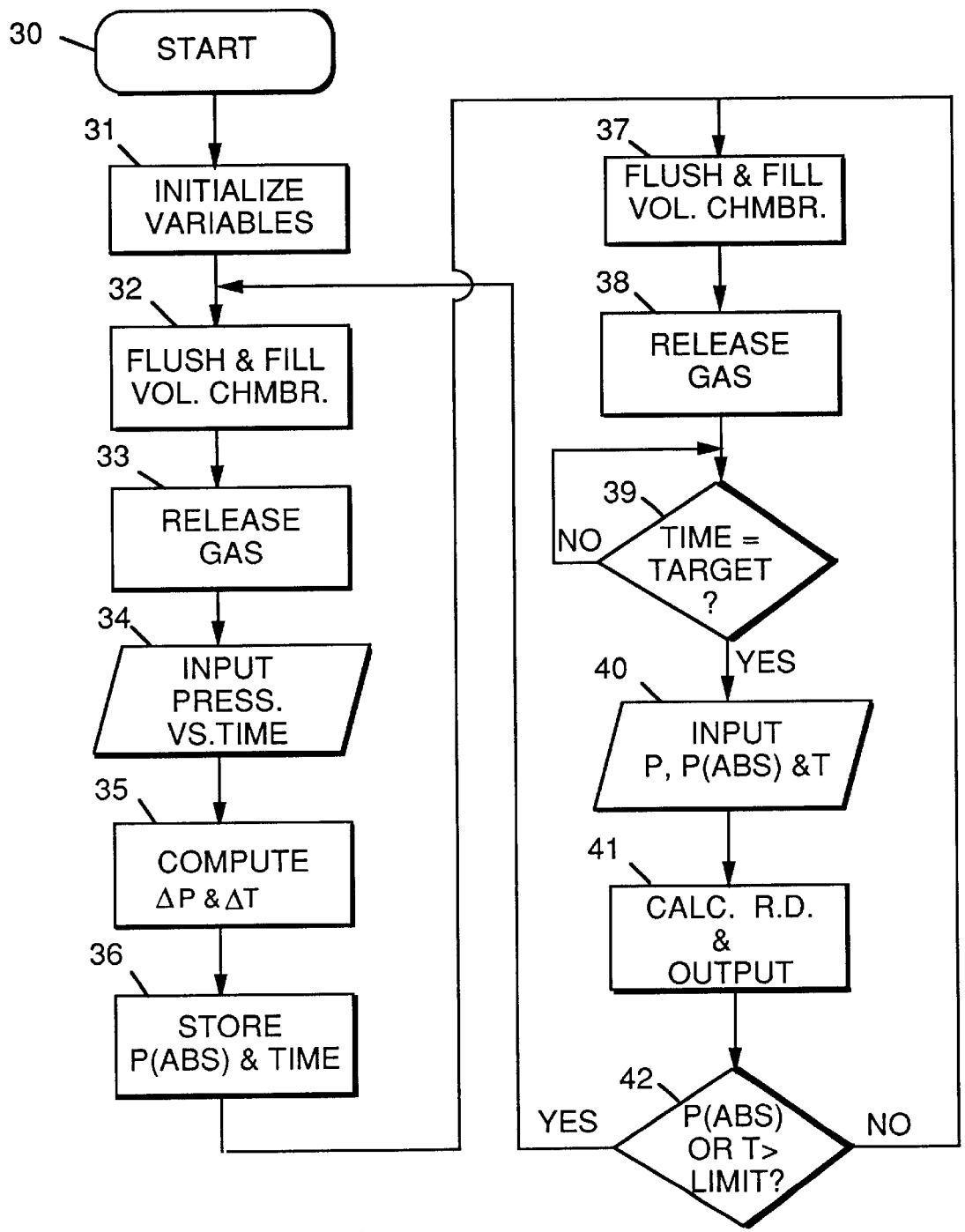
FIG. 3 is a flow chart of the operation of a microcontroller in the apparatus of FIGS. 1 and 2.

The microcontroller 15 includes a processor, and sufficient random access memory (RAM) and programmable read only memory (PROM) for storage and execution by the processor of a control program to carry out the method of the invention as diagrammed in FIG. 3. The microcontroller 15 also includes both analog and digital I/O (inputs and outputs). These include a 4–20 milliamp analog output 21 and an RS-232 serial data output 22.

As represented in FIG. 3, after the start of the program execution represented by start block 30, the apparatus 10 is operated for a reference gas cycle represented by blocks 32–37 and a sample gas cycle represented by blocks 39–41. Prior to the reference gas cycle, any necessary program parameters are initialized as represented by process block 31. Included in process block 31 is the computation of the pre-selected reference gas pressure from factory calibration data. As represented by process block 32, volume chamber 20 is filled with a volume of reference gas by opening valve 11, and then closing valve 11 under control of the microcontroller 15.

Then, the processor in the microcontroller 15 executes program instructions represented by block 33 which forces the release of gas from the volume chamber. During the release of the gas, the microcontroller 15 stores the individual samples of the volume chamber pressure and the elapsed time of the gas release into its memory, as represented by input block 34.

Next, the microcontroller 15 executes instructions represented by block 35 and searches the recorded data stream to find a target pressure for the reference gas and then find the associated elapsed time required to achieve that target pressure. The microcontroller 15 also reads and stores the barometric pressure and the gas temperature corresponding to the conditions during this reference cycle as represented in block 36.

Block 37 begins the sample measurement cycle. The volume chamber is flushed and filled with sample gas and then the release of the sample gas is initiated as represented in block 38. The time of discharge is monitored until the elapsed time is equal to that time recorded during the reference gas cycle. This decision function is represented in block 39. When the elapsed time is equal to the reference gas elapsed time, the volume chamber pressure is recorded as well as the barometric pressure and gas temperature, as represented in input block 40.

The relative density of the sample gas is calculated and any output signals are updated as represented in block 41. Block 42 is executed to determine whether a new sample cycle or a new reference cycle must be undertaken. If either the barometric pressure or the gas temperature has changed significantly, then a new reference cycle must be undertaken, otherwise the sampling cycle can be continued.

Pre-calibration of the reference gas pressure referred to previously is a one time calibration activity invoked by replacing the sample gas in FIG. 1 with a second gas of known relative density. For gases with relative density greater than unity, carbon dioxide is used as a second known gas. For the lower density gas such as natural gases, methane is preferred as a reference gas and the second gas is usually a certified and dilute mixture of methane and carbon dioxide or nitrogen or even a small amount of propane. This second reference gas and the first reference gas are alternately measured and a gage pressure ratio is computed for a selected time of discharge that is the same for both gases. When this ratio of gage pressures between the second gas and the reference gas is in the same ratio as the relative densities for the gases, then a ratio of reference gas gage pressure to its initial chamber gage pressure is computed and this becomes the calibration pressure ratio for the particular volume chamber and flow pore combination. This calibration pressure ratio is normally stored in a non-volatile memory for continued use.

When a reference gas cycle is operated, this calibration pressure ratio and the initial chamber gage pressure are used to determine the elapsed time required for the reference gas to reach this discharge pressure. That elapsed time becomes the short term identifier for measuring sample gas during its measurement discharge.

The rate of reference gas cycle usage can be selected from one to many cycles of the sample gas. If, however, either sample gas temperature or barometric pressure changes significantly, then the elapsed time determined by a previous reference gas cycle will produce an incorrect measurement and a new reference cycle must be employed to determine a new elapsed time. Fortunately, changes in barometric pressure or gas temperatures produce small effects. Tolerances of 0.25 in. Hg in barometric pressure and temperature changes as large as 10° C. are tolerable.

When the blending supply gas propane is contaminated with significant amounts of butane, a common occurrence in certain regions of the world, errors in the computation of Wobbe Index are introduced because the relationship between heating value and relative density is uncertain. Measuring the supply gas under those circumstances corrects most of the introduced errors.

Figure 2:
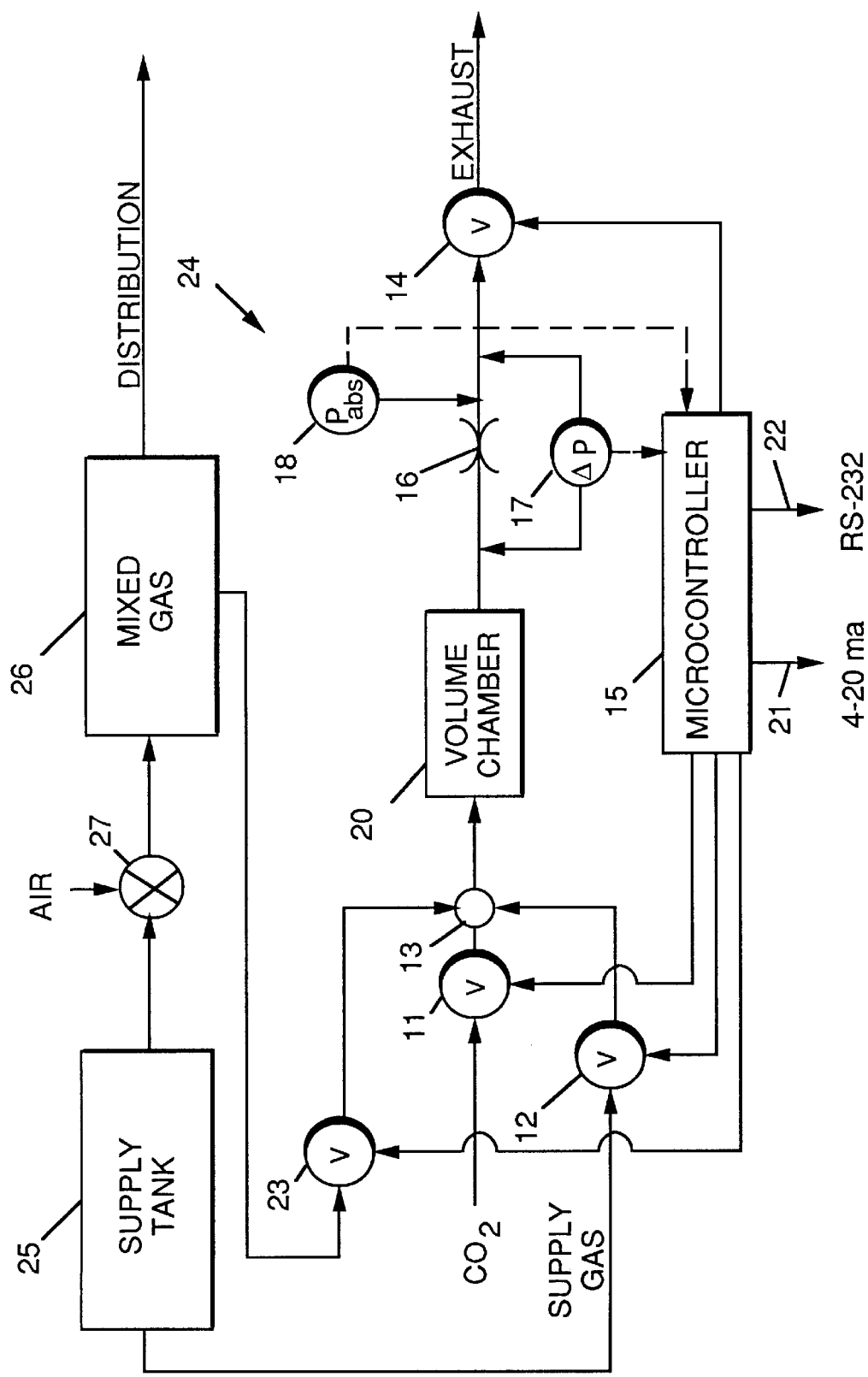
FIG. 2 is a block diagram of a modified form of the apparatus of FIG. 1.

FIG. 2 shows a modified apparatus of FIG. 1 connected to a supply tank 25 which contains a gas to be mixed for supply in a local distribution system. A sample line connects the supply tank 25 to the supply gas input through valve 12. As part of a blending device, a mixing valve 27 is connected in a line between the outlet of supply tank 25 and an inlet on a tank with mixed gas to be distributed in the local distribution system. The mixing valve 17 allows air to be added or reduced in the mixture flowed into storage tank 26. A sample line connects the storage tank of mixed gas to another of the inputs on apparatus 24, so that a sample of the mixed gas 26 can be introduced in volume chamber 20 and then released to measure relative density. Another input receives a supply of carbon dioxide or air as a reference gas. In this embodiment, the microcontroller 15 executes a program to test a sample from the supply tank in the same manner as described for FIG. 1. The microcontroller 15 would then provide a signal which can be used by the blending system to control the supply of air introduced through mixing valve 27. A sample from the tank of mixed gas 26 could then be tested to close the control loop for blending of air in the mixture. In this way, the present invention is applied to control the mixture gas as it is being distributed for consumption.

This has been a description of examples of how the invention can be carried out. Those of ordinary skill in the art will recognize that various details may be modified in arriving at other detailed embodiments, and these embodiments will come within the scope of the invention.

Therefore, to apprise the public of the scope of the invention and the embodiments covered by the invention, the following claims are made.

We claim:

1. A method for measuring the relative density of a gas, the method comprising:

flowing a reference gas and a sample gas from a volume chamber through an orifice that is sized to be small relative to a connecting line and sized with respect to an initial pressure of the reference gas and the sample gas, respectively, such that the effects of a discharge coefficient of the orifice are not necessary to a computation of relative density;

measuring an elapsed time of discharge when the reference gas reaches a target discharge pressure;

measuring the pressure of the sample gas across the orifice at the elapsed time of discharge determined for the reference gas; and computing the relative density of a sample gas from a known relative density of a reference gas, from predetermined constants for the reference gas and the sample gas, respectively, and from a ratio of the pressure of the sample gas across the orifice to the pressure of the reference gas across the orifice.

2. The method of claim 1, wherein an initial pressure of gas released through said orifice is determined according to an identity of the reference gas and is in a range from about 1 to about 6 psig.

3. The method of claim 1, wherein the sample gases are natural gases or are mixtures including at least one of the gases methane, propane or butane, and wherein the reference gas has a pressure ratio of target discharge pressure to initial pressure between 0.05 and 0.35.

4. The method of claim 1, further comprising the step of determining the target discharge pressure for the reference gas from a calibration pressure ratio of discharge pressure to initial pressure for the reference gas determined from a calibration cycle and determined from said initial pressure for the reference gas in the volume chamber.

5. The method of claim 4, wherein the calibration cycle further comprises the step of alternately discharging the first-mentioned reference gas and a second reference gas from a known initial pressure, and determining the calibration ratio when the discharge pressures of the first-mentioned reference gas and the second reference gas at a common elapsed time are proportional to a ratio of their respective known relative densities.

6. The method of claim 1, wherein the reference gas is air, carbon dioxide or methane.

7. The method of claim 1, wherein the orifice is a pore in a range from at about 0.0012 inches to about 0.0047 inches in diameter.

8. The method of claim 1, wherein the pore is mounted in a structure having a diameter at least three times that of the diameter of the pore.

9. The method of claim 1, further comprising the step of initiating a reference gas cycle in response to changes of selected magnitude in either atmospheric pressure or in temperature of the sample gas.

10. The method of claim 1, further comprising the step of adjusting the frequency of reference gas cycling between one and a selected number of sample gas cycles.

11. The method of claim 1, wherein the sample gas is a sample of a mixture including a supply gas that is distributed in a gas distribution system and further comprising the step of adding a gas to adjust relative density of the mixture that includes the supply gas.

12. The method of claim 1, further comprising the step of controlling the initial pressure of the reference gas and the sample gas.

13. An apparatus for measuring the relative density of a gas, the apparatus comprising:

an orifice having a pore that is sized to be small relative to a connecting line and sized with respect to an orifice inlet pressure of the gas such that the effects of an orifice discharge coefficient are not necessary to a computation of relative density;

a chamber of non-varying volume for holding gas at a preselected pressure, said chamber communicating with said connecting line to said orifice;

means for supplying a reference gas to said chamber;

means for supplying a sample gas to said chamber;

a valve for controlling release of gas from said chamber to said orifice;

a pressure transducer for measuring a difference in pressure across said orifice;

at least one memory for storing program instructions; and a processor for receiving signals from said the pressure transducer, wherein said processor executes program instructions for computing relative density of a sample gas released from said chamber through said orifice based on a known relative density of a reference gas, and pressure measurements made for the reference gas and the sample gas, respectively, corresponding to a common elapsed time period, as each is released from said chamber through said orifice.

14. The apparatus of claim 13, wherein the reference gas is air, carbon dioxide or methane.

15. The apparatus of claim 13, wherein the pore has a diameter from about 0.0012 to about 0.0047 inches.

16. The apparatus of claim 13, wherein the pore is mounted in a structure having a diameter at least three times that of the diameter of the pore.

17. The apparatus of claim 13, wherein the processor executes further program instructions for adjusting the frequency of reference gas cycling from one to a selected number of cycles of the sample gas.

18. The apparatus as in claim 13, wherein the sample gas is a sample of a mixture including a supply gas which is distributed through a gas distribution system and further comprising means for adjusting composition of the mixture to adjust relative density of the mixture.

19. The apparatus of claim 13, wherein the processor further includes means responsive to changes in either barometric pressure or in temperature of the sample gas for initiating a reference gas cycle.

20. An apparatus for measuring the relative density of a gas, the apparatus comprising:

an orifice having a pore that is sized to be small relative to a connecting line and sized with respect to an orifice inlet pressure of the gas such that the effects of an orifice discharge coefficient are not necessary to a computation of relative density;

a chamber of non-varying volume for holding gas at a preselected pressure, said chamber communicating with said connecting line to said orifice;

means for supplying a reference gas to said chamber;

means for supplying a sample gas to said chamber;

a valve for controlling release of gas from said chamber to said orifice;

a pressure transducer for measuring a difference in pressure across said orifice;

a processor for receiving signals from said pressure transducer, wherein said processor executes program instructions for computing relative density of a sample gas released from said chamber through said orifice based on a known relative density of a reference gas, and pressure measurements made for the reference gas and the sample gas as each is released from said chamber through said orifice; and wherein an initial pressure of gas released from said chamber is from about 1 to about 6 psig.

21. An apparatus for measuring the relative density of a gas, the apparatus comprising:

an orifice having a pore that is sized to be small relative to a connecting line and sized with respect to an orifice inlet pressure of the gas such that the effects of an orifice discharge coefficient are not necessary to a computation of relative density;

a chamber of non-varying volume for holding gas at a preselected pressure, said chamber communicating with said connecting line to said orifice;

means for supplying a reference gas to said chamber;

means for supplying a sample gas to said chamber;

a valve for controlling release of gas from said chamber to said orifice;

a pressure transducer for measuring a difference in pressure across said orifice;

a processor for receiving signals from said pressure transducer, wherein said processor executes program instructions for computing relative density of a sample gas released from said chamber through said orifice based on a known relative density of a reference gas, and pressure measurements made for the reference gas and the sample gas as each is released from said chamber through said orifice; and wherein the sample gas is a mixture that includes methane or a mixture that includes propane or butane, and wherein the reference gas has a pressure ratio of measurement pressure to the initial chamber pressure of between 0.05 and 0.35.

22. An apparatus for measuring the relative density of a gas, the apparatus comprising:
- an orifice having a pore that is sized to be small relative to a connecting line and sized with respect to an orifice inlet pressure of the gas such that the effects of an orifice discharge coefficient are not necessary to a computation of relative density;
- a chamber of non-varying volume for holding gas at a preselected pressure, said chamber communicating with said connecting line to said orifice;
- means for supplying a reference gas to said chamber;
- means for supplying a sample gas to said chamber;
- a valve for controlling release of gas from said chamber to said orifice;
- a pressure transducer for measuring a difference in pressure across said orifice;
- at least one memory for storing program instructions; and
- a processor for receiving signals from said the pressure transducer, wherein said processor executes program instructions for computing relative density of a sample gas released from said chamber through said orifice based on a known relative density of a reference gas, and pressure measurements made for the reference gas and the sample gas, respectively, corresponding to a common elapsed time period, as each is released from said chamber through said orifice; and further comprising means for introducing a second reference gas for calibration of the apparatus relative to the first reference gas.

* * * * *